(12) United States Patent
Thompson et al.

(10) Patent No.: US 8,281,788 B2
(45) Date of Patent: *Oct. 9, 2012

(54) CARDIOPULMONARY RESUSCITATION DEVICE

(76) Inventors: Darrel K. Thompson, Memphis, TN (US); Phyllis D. Thompson, Memphis, TN (US)

(*) Notice: Subject to any disclaimer, the term of this patent is extended or adjusted under 35 U.S.C. 154(b) by 164 days.

This patent is subject to a terminal disclaimer.

(21) Appl. No.: 12/574,480

(22) Filed: Oct. 6, 2009

(65) Prior Publication Data

US 2010/0087760 A1   Apr. 8, 2010

Related U.S. Application Data

(63) Continuation-in-part of application No. 11/327,278, filed on Jan. 6, 2006, now Pat. No. 7,806,118, which is a continuation-in-part of application No. 10/820,239, filed on Apr. 6, 2004, now Pat. No. 7,032,596.

(60) Provisional application No. 61/103,094, filed on Oct. 6, 2008.

(51) Int. Cl.
| | |
|---|---|
| *A61M 15/00* | (2006.01) |
| *A61M 16/00* | (2006.01) |
| *A61G 10/00* | (2006.01) |
| *A61H 31/00* | (2006.01) |
| *A61H 7/00* | (2006.01) |

(52) U.S. Cl. ......... 128/205.13; 128/200.24; 128/204.18; 128/202.12; 128/205.26; 601/41; 601/42; 601/43; 601/44; 601/149; 601/150; 601/151; 601/152

(58) Field of Classification Search ............. 128/200.24, 128/204.18, 202.12, 205.26; 601/41–44, 601/149–152
See application file for complete search history.

(56) References Cited

U.S. PATENT DOCUMENTS

| | | | |
|---|---|---|---|
| 3,046,978 A * | 7/1962 | Lea | ......................... 128/205.13 |
| 3,882,860 A | 5/1975 | Frimberger | |
| 4,374,521 A | 2/1983 | Nelson et al. | |
| 4,440,163 A | 4/1984 | Spergel | |
| 4,532,923 A | 8/1985 | Flynn | |
| 4,821,712 A | 4/1989 | Gossett | |
| 4,919,132 A | 4/1990 | Miser | |

(Continued)

OTHER PUBLICATIONS

Jay, G.D., 2003,CPR effectiveness in microgravity: comparison of three positions and a Mechanical Device, Aviation, Space, and Environmental Medicine, vol. 74, No. 11, p. 1183-1189.

*Primary Examiner* — Patricia Bianco
*Assistant Examiner* — Nihir Patel
(74) *Attorney, Agent, or Firm* — Harris, Shelton, Hanover & Walsh (57) ABSTRACT

A cardiopulmonary resuscitation device that combines ventilation of a patient's lungs with chest compressions on the patient's sternum area. The device includes a self-inflating bag having a flat top side as a proper position on the self-inflating bag for applying force to the top side of the self-inflating bag, a flat bottom side on the self-inflating bag for properly positioning the bag on the patient's sternum area, an outlet port through which the content of the bag is forced when the flat top side of the bag is pushed toward the flat bottom side of the bag, a connector connecting the bag with a tube extending from the outlet port, a headband face mask for placement over the patient's mouth and nose, and a second connector positioned between the tube and the face mask.

12 Claims, 5 Drawing Sheets

U.S. PATENT DOCUMENTS

| | | | |
|---|---|---|---|
| D321,418 S | 11/1991 | Dolida et al. | |
| 5,163,424 A | 11/1992 | Kohnke | |
| D335,552 S | 5/1993 | Kohnke | |
| 5,427,091 A | 6/1995 | Phillips | |
| 5,483,955 A | 1/1996 | Morris | |
| 5,492,114 A * | 2/1996 | Vroman | 128/205.13 |
| 5,540,221 A | 7/1996 | Kaigler et al. | |
| 5,647,354 A | 7/1997 | Lakhani et al. | |
| 5,791,340 A | 8/1998 | Schleufe et al. | |
| 5,803,074 A | 9/1998 | Pope | |
| 5,842,467 A | 12/1998 | Greco | |
| 5,996,579 A | 12/1999 | Coates et al. | |
| 6,058,933 A | 5/2000 | Good et al. | |
| 6,062,219 A | 5/2000 | Lurie et al. | |
| 6,098,621 A | 8/2000 | Esnouf | |
| 6,123,075 A | 9/2000 | Kirk | |
| 6,276,363 B1 | 8/2001 | Gray | |
| 6,340,023 B2 | 1/2002 | Elkins | |
| 6,527,011 B1 * | 3/2003 | Mantz | 137/848 |
| 6,539,941 B2 | 4/2003 | Haubeil | |
| 6,568,388 B2 | 5/2003 | Christopher | |
| 6,578,574 B1 | 6/2003 | Kohnke | |
| 6,631,713 B1 | 10/2003 | Christopher | |
| 6,648,841 B1 | 11/2003 | Sessler | |
| 6,745,769 B2 | 6/2004 | Klempau | |
| 6,763,831 B2 | 7/2004 | Sniadach | |
| 6,776,160 B2 | 8/2004 | Wang | |
| 6,792,947 B1 | 9/2004 | Bowden | |
| 6,988,499 B2 | 1/2006 | Holt | |
| 7,938,115 B2 * | 5/2011 | Thompson et al. | 128/205.13 |

* cited by examiner

CARDIOPULMONARY RESUSCITATION DEVICE

RELATED APPLICATIONS:

This application incorporates by reference in its entirety and claims priority under 35 U.S.C. Section 119(e) to U.S. provisional patent application Ser. No 61/103,094 filed Oct. 6, 2008; This application is a continuation-in-part of and claims priority under 35 U.S.C. Section 120 to U.S. patent application Ser. No. 11/327,278 filed Jan. 6, 2006, now U.S. Pat. No. 7,806,118 which claims priority and is a continuation-in-part to U.S. patent application Ser. No. 10/820,239 filed Apr. 6, 2004, now U.S. Pat. No. 7,032,596 (hereby incorporated by reference)

BACKGROUND OF THE INVENTION

1. Field of the Invention

The present invention relates, in general, to a device that uses a squeeze bag-type resuscitator in a manner that incorporates cardiopulmonary Resuscitation (CPR) type chest compressions.

2. Background Art

Two general emergency procedures used when a patient's normal breathing has been disrupted are the use of self-inflating, squeeze bag resuscitators and cardiopulmonary resuscitation (CPR). Self-inflating, squeeze bag resuscitators are commonly used for artificial, emergency ventilation of a patient's lungs to revive the patient when normal breathing has been disrupted, but the patient's heart is still beating. Several types of such self inflating, squeeze bag resuscitators are in wide use, and are sometimes referred to as respirators. The typical self-inflating, squeeze bag resuscitator consists, in general, of an airtight face mask that fits over the patient's nose and mouth, and a self-inflating bag connected to the face mask. When the bag is squeezed, air or oxygen is forced from the bag into the patient's lungs. The bag re-inflates automatically when released, drawing atmosphere air, etc., into the bag through a bag fill valve (a one way, inward flow check valve) typically located at the end of the bag opposite from the face mask. Air from the lungs leaves the mask by some type of escape valve (often referred to as a nonrebreathing or NRB valve) without returning to the bag. Cardiopulmonary resuscitation (CPR) is administered when a patient stops breathing and the patient's heart stops beating, due to sudden cardiac arrest or the like. CPR includes mouth-to-mouth breathing, and chest compression. To perform mouth-to-mouth breathing, the patient's nose is pinched shut and the rescuer blows directly into the patient's mouth. After mouth-to-mouth breathing, the rescuer then performs chest compression by pushing down on the patient's chest right between the nipples (i.e., the sternum area). Nothing in the known prior art, either singly or in combination, discloses or suggests the present invention.

BRIEF SUMMARY OF THE INVENTION

The present invention discloses a device that uses a squeeze bag-type resuscitator in a manner that allows a rescuer to combine artificial, emergency ventilation of a patient's lungs with cardiopulmonary resuscitation (CPR) type chest compressions. More specially, device includes: a self-inflating bag having a non-rigid flat top side, a non-rigid flat bottom side for contacting the patient's sternum area wherein the self-inflating bag does not include a bag-fill value; an outlet port through which the content of the self inflating bag is forced when the top side of the self-inflating bag is pushed toward the bottom side of the self-inflating bag, a first connector connecting the bag with a tube extending from the outlet port of the self-inflating bag to the face mask, a face mask for placement over the patient's mouth and nose, and indicator means contacting the self-inflating bag for placement over the patient's sternum area and for providing an indication of the amount of force being applied through top and bottom sides of the self-inflating bag to the patient's chest by the bottom side during chest compressions on the patient's sternum area when the top side of the self-inflating bag is pushed toward the bottom side of the self inflating bag. In this device the bag-fill-valve can be positioned on the first connector in one embodiment or in an alternative embodiment on the face mark. The cardiopulmonary resuscitation device can also include a second connector positioned between the tube and the face mask. The second connector is flexible. The second connector includes a duck-bill to prevent spent air from the patient lungs from entering the air tube. The second connector can also include an escape valve through which the spent air from the patient to escape into the atmosphere.

Figure 1:
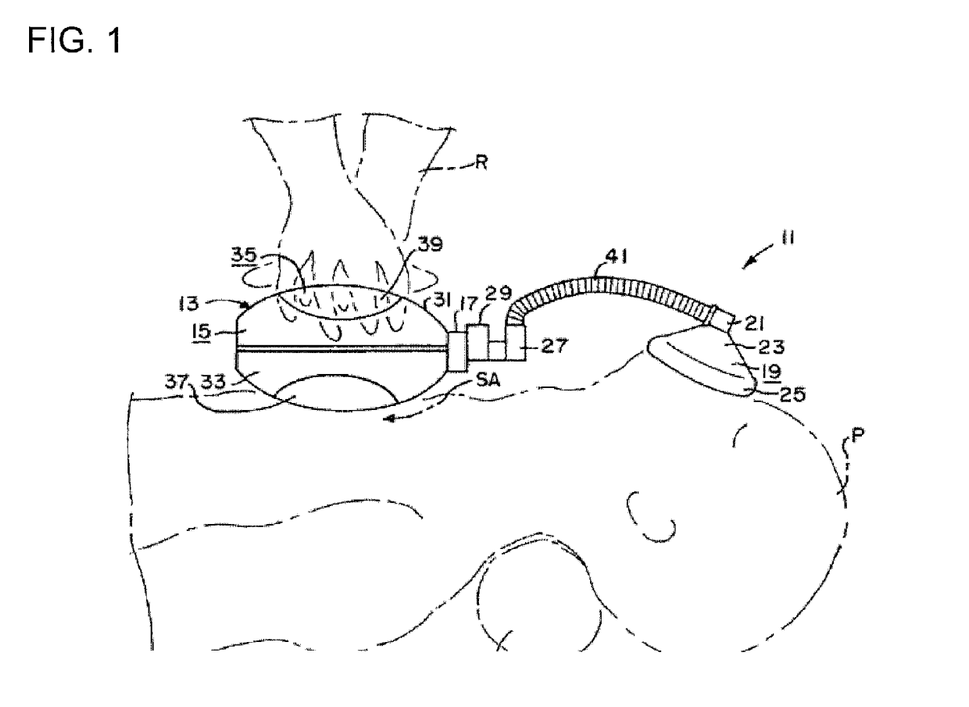
FIG. 1 is diagrammatic view of a first embodiment of the cardiopulmonary resuscitation device of the present invention, shown with the face mask thereof placed over a patient's mouth and nose, and with the self-inflating bag thereof placed on the patient's chest with the target indicia on the self-inflating bag positioned over the patient's sternum area.
Figure 2:
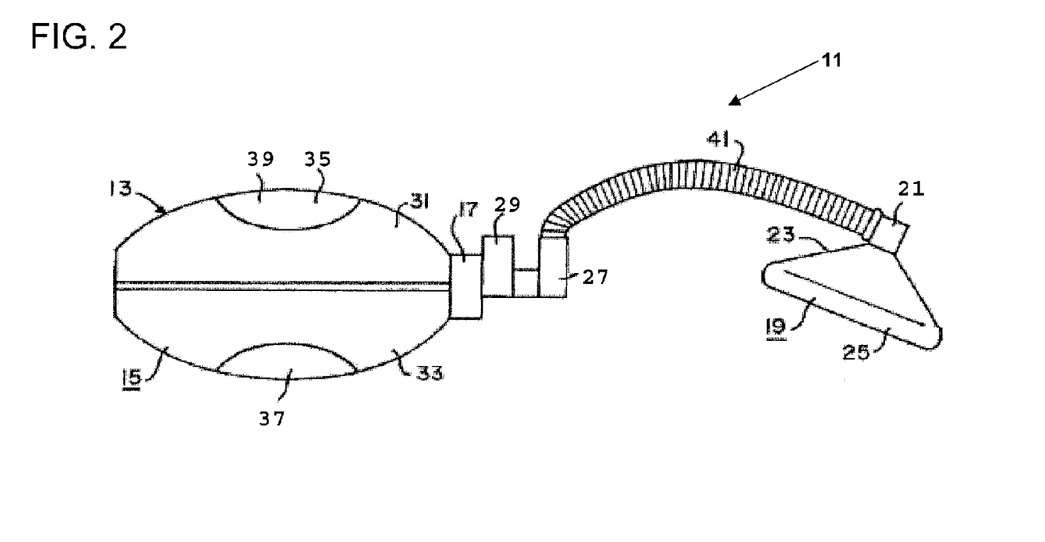
FIG. 2 is a side elevational view of the cardiopulmonary resuscitation device of FIG. 1.

DETAILED DESCRIPTION OF THE INVENTION:

A first embodiment of the cardiopulmonary resuscitation device of the present invention is shown generally in FIGS. 1-2, and identified by the numeral 11. The device 11 uses a modified squeeze bag-type resuscitator 13 in a manner that allows a user/rescuer R to help or rescue a patient P by combining artificial, emergency ventilation of the patient's lungs with cardiopulmonary resuscitation (CPR) type chest compressions on the patient's sternum area SA.

The squeeze bag-type resuscitator 13 preferably includes a typical self-inflating squeeze bag 15 constructed so that when the bag 15 is squeezed or otherwise compressed, air or oxygen is forced from the interior of the bag 15 out some type of outlet port or connector 17 for allowing the squeeze bag 15 to be connected to other parts of the resuscitator 13, e.g., to a face mask 19 for placement over a patient's mouth and nose. The face mask 19 (sometimes called a face-piece) typically includes a mount 21 for connection to the squeeze bag 15 or the like and a body 23 with a seal member 25 about the edge thereof to allow a substantially air-tight seal to be formed between the face mask 19 and the patient's face. The face mask 19 may also include an elastic head band or the like (not shown) for securing the body 23 thereof to the patient's face. The resuscitator 13 typically includes some type of escape valve 27 (often referred to as a nonrebreathing or NRB valve) mounted between the outlet port or connector 17 of the bag 15 and the face mask 19 so that after the face mask 19 is placed over the patient's mouth and nose, air from the patient's lungs will leave the face mask 19 through the escape valve 27 without returning to the bag 13. When the bag 15 is released, etc., it will re-inflate automatically, drawing atmosphere air, etc., into the bag through a bag fill valve 29 (i.e., a one way, inward flow check valve) that is combined with the bag 15 in communication with the interior thereof by being coupled to the connector 17 or attached directly to the bag 15, often at the end of the bag 15 directly opposite from the connector 17. While the shape and size of the bag 15 can vary as will now be apparent to those skilled in the art, in general, the bag 15 has one side that can be designated as the top side 31 and another side that can be designated as the bottom side 33.

The device 11 of the present invention includes target indicia 35 on the self-inflating bag 13 to indicate the proper position of the self-inflating bag 15 on the patient's sternum area SA and to indicate the proper location on the self-inflating bag 15 for applying force to the top side 31 of the self-inflating bag 15 in order to perform artificial, emergency ventilation of the patient's lungs followed by cardiopulmonary resuscitation (CPR) type chest compressions on the patient's sternum area SA. The target indicia 35 preferably includes a bottom target indicia 37 on the bottom side 33 of the self-inflating bag 15 to indicate the proper position of the self-inflating bag 15 on the patient's sternum area SA, and preferably includes a top target indicia 39 on the top side 31 of the self-inflating bag 15 to indicate the proper location on the self-inflating bag 15 for applying force to the top side 31 of the self-inflating bag 15 in order to perform artificial, emergency ventilation of the patient's lungs followed by cardiopulmonary resuscitation (CPR) type chest compressions on the patient's sternum area SA. While the specific construction, shape and size of the bottom and top target indicia 37, 39 can vary as will now be apparent to those skilled in the art, each bottom and top target indicia 37, 39 may consist merely of a visually and/or tactually distinctive, circular shaped decal, piece of tape, etc., attached to the appropriate surface of the bag 15.

The device 11 of the present invention includes a tube 41 extending from the outlet port 17 of the self-inflating bag 15 to the face mask 19 so that air forced out of the bag 13 through the outlet port 17 thereof will pass to the face mask 19 and into the patient's lungs when the face mask 19 is placed over the patient's mouth and nose. The tube 41 is preferably elongated and flexible for allowing the self-inflating bag 15 to be positioned over the patient's sternum area SA while the face mask 19 is placed over the patient's mouth and nose. While the exact size, length and construction of the tube 41 may vary as will now be apparent to those skilled in the art, the tube 41 may be constructed out of typical, medical grade, flexible plastic hose sized to fit the mount 21 of the face mask 19 and the escape valve 27, and long enough to extend between the patient's sternum area SA and face while allowing the bag 15 to be properly positioned on the patient's sternum area SA with the face mask 19 properly positioned simultaneously over the patient's nose and mouth. The tube 41 is preferably designed to retrofit through adaptable connectors any standard tracheobronchial tree or bronchial tube. This will allow a user/rescuer R to administer to the patient P who has been injected with a tracheobronchial tree or bronchial tube with the same method of cardiopulmonary resuscitation without the face mask 19.

The method of using the cardiopulmonary resuscitation device 11 of the present invention includes the step of first providing a cardiopulmonary resuscitation device 11 including a self-inflating bag 15, target indicia 35. on the self-inflating bag 15 to indicate the proper position of the self-inflating bag on the patient's sternum area SA and to indicate the proper location on the self-inflating bag 15 for applying force to the top side 31 of the self-inflating bag 15, a face mask 19 for placement over the patient's mouth and nose, and a tube 41 extending from the outlet port 17 of the self-inflating bag 15 to the face mask 19, The patient P is placed in a normal cardiopulmonary resuscitation position, preferably supine with a neck support NS for maintaining the patient's airway open during resuscitation. The face mask 19 of the cardiopulmonary resuscitation device 11 is placed over the patient's mouth and nose, and the self-inflating bag 15 of the cardiopulmonary resuscitation device 11 is placed on the patient's chest with the target indicia 35 on the self-inflating bag 15 positioned over the patient's sternum area SA.

The user/rescuer R can then apply force to the target indicia 35 on the self-inflating bag of the cardiopulmonary resuscitation device 11 to first force air from the self-inflating bag 15 through the tube 41 and the face mask 19 into the patient's lungs to ventilate the patient's lungs (often referred to as a rescue breath), and then to compress the patient's sternum area SA (often referred to as a chest compression). After thus applying force to the target indicia 35 on the self-inflating hag 15 of the cardiopulmonary resuscitation device 11, the user/rescuer R releases the self-inflating bag 15, and the bag 15 reinflates by drawing atmosphere air into the bag 15 through the bag fill valve 29, while air from the patient's lungs will pass to atmosphere through the escape valve 27. These cardiopulmonary resuscitation steps can be repeated as necessary. Typically the user/rescuer R will apply a number of chest compressions after a single forced ventilation (rescue breath) by applying a number of chest compressions before fully releasing the self-inflating bag 15) so that the ratio of chest compressions to forced ventilations equal a desired number (e.g., 15 to 30 chest compressions per two forced ventilations at a rate of 80 to 100 compressions a minute). The cardiopulmonary resuscitation device 11 may include pressure sensors (not shown) to monitor chest compressions, and an audible means (not shown) that will orally walk a user/rescuer R through the steps of CPR using the device.

A second embodiment or modified version of the cardiopulmonary resuscitation device of the present invention is shown generally in FIGS. 3-10 and identified by the numeral 201. The cardiopulmonary resuscitation device 201 is substantially identical to the cardiopulmonary resuscitation device 11 and the above disclosure of the cardiopulmonary resuscitation device 11 should be consulted for a detailed understanding of the construction and operation of the cardiopulmonary resuscitation device 201 and the same reference numerals and characters will be used for like components of the cardiopulmonary resuscitation device 201 as herein used for the cardiopulmonary resuscitation device 11. However, as shown in FIGS. 3-6, the cardiopulmonary resuscitation device 201 includes a self-inflating bag 15 with a handle 120, a non rigid-flat top side 121 and a non rigid-flat bottom side 122. The back end of the self-inflating bag 15 of the cardiopulmonary resuscitation device 201 is closed and will not allow any air to enter or escape.

Figure 7:
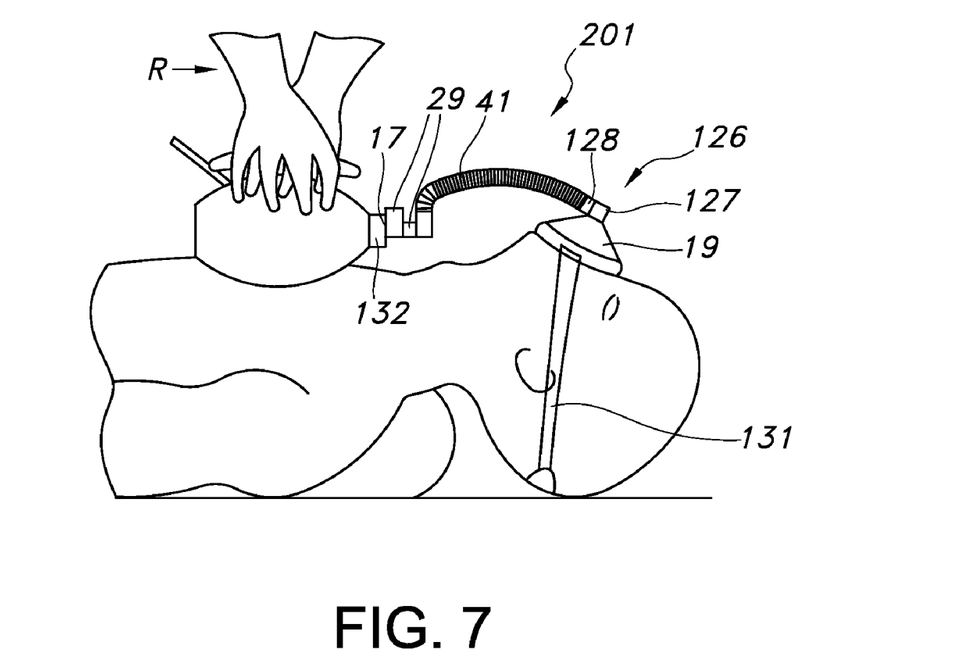
FIG. 7 is a diagrammatic view of a second embodiment of the cardiopulmonary resuscitation device of the present invention, shown with the face mask thereof placed over a patient's mouth and nose, and with the self-inflating bag thereof placed on the patient's chest with the target indicia on the self-inflating bag positioned over the patient's sternum area.
Figure 8:
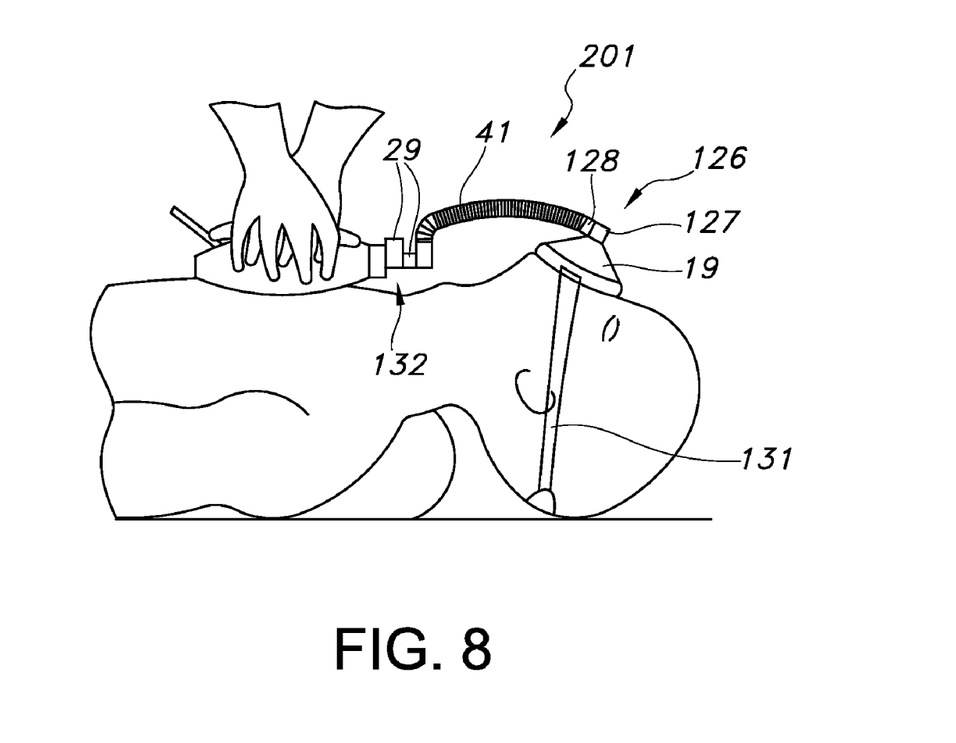
FIG. 8 is a diagrammatic view somewhat similar to FIG. 7 but with a rescuer compressing the self-inflating bag to ventilate the patient's lungs and compress the patient's sternum area.
Figure 10:
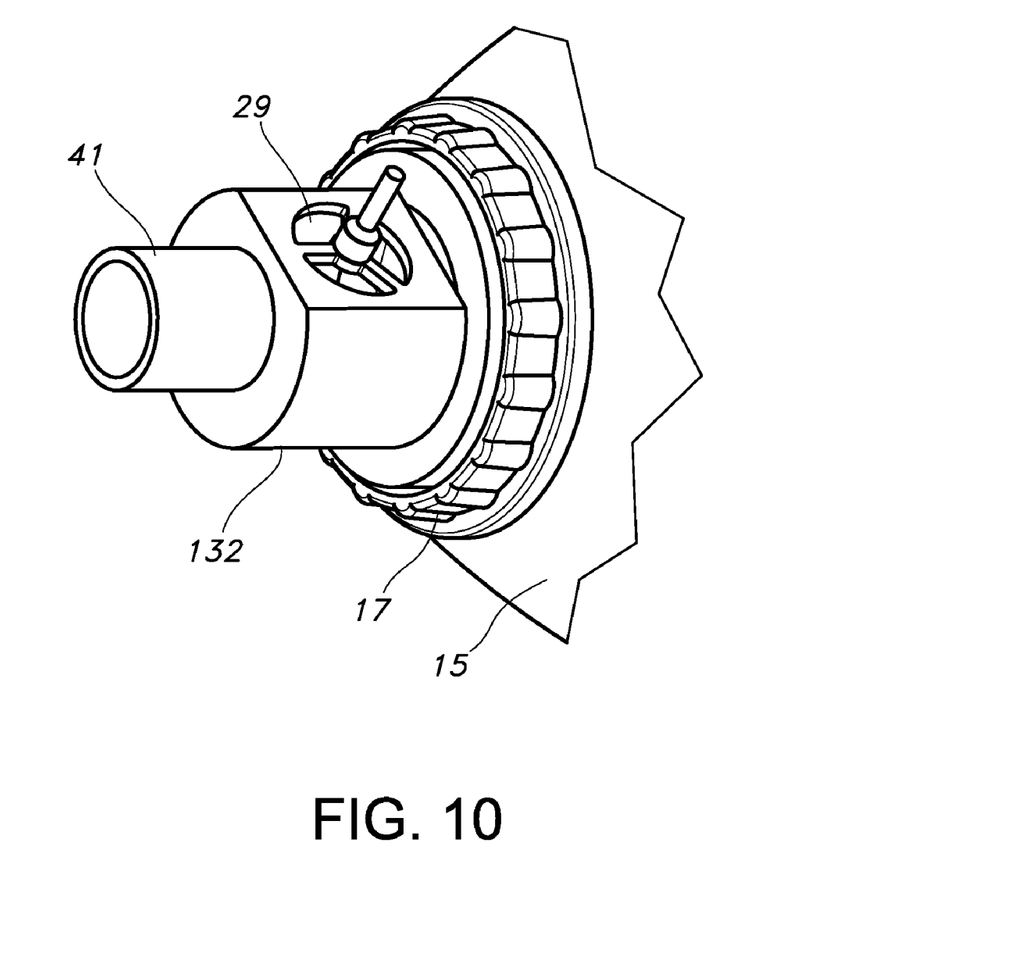
FIG. 10 is a schematic drawing of an embodiment of the first connector.

FIGS. 7, 8 and 10 further show a first connector and identified by the numeral 132. The first connector 132 is attached the front end of the self-inflating bag 15 and it can be screwed on to the bag 15 of the cardiopulmonary resuscitation device 201. The first connector 132 has two embodiments.

Now referring to FIG. 10, the first embodiment of the connector 132 has a circler bag-fill-valve 29 attached to the connector 132 and located on the base of the connector 132. The outlet port 17 is also located on the base of the first connector 132 which is attached to the bag 15. The bag-fill-valve 29 allows atmosphere air to enter the self-inflating resuscitator bag 15 and prevents that same atmosphere air from escaping from the bag-fill-valve 29 when the bag 15 is squeezed. Duck bill valve 128 located in the second connector 126 keeps the atmosphere air in the bag 15 after it is filled. The duck bill valve 128 remains closed to prevent the air from escaping the bag 15 until outer force (squeezed) is applied to the bag 15. That force causes the duck bill valve 128 in the second connector 126 to open and allow the atmosphere air to exit the resuscitator bag 15 and pass the air tube 41 to reach the head band 131 facemask 19 and into the patient's lungs. When pressure is applied through the resuscitator bag 15 to perform chest compression, the escape valve 127 located in the second connector 126 will allow spent air from the patient lungs to escape into the atmosphere after the duck bill valve 128 blocks the spent air from traveling into the air tube 41.

The second embodiment of the first connector 132 has two circular bag-fill-valve 29 attached to the connector 132 and located on the of the connector 132, one on opposite sides of the shaft (not shown here) of the connector 132. The shaft is design as part of the exit port that is attached to the extended air tube 41 that is attached to the second connector 126 that is attached to the headband 131 facemask 19. The two bag-fill-valve/inlet valve works the same as described in the first embodiment of the connector 132. They allow atmosphere air to enter the bag 15 and when the bag is squeezed the air exit the bag through the exit port down the air tube, into the second connector 126, the headband facemask and the patent lungs. The bag-fill-valve/inlet valve 29 are design as a one way valve which prevent air from escaping from the device/bag but allows air to enter the bag when the bag is released.

Further, as shown in FIGS. 7 and 8, the cardiopulmonary resuscitation device 201 includes a second connector 126 which is located between the facemask 19 and the tube 41. The second connector 126 is preferably flexible and air tight. The second connector 126 can be made of a flexible material such as rubber or a compliant plastic, or alternatively the second connector 126 can be mechanical, such as, but not limited to a ball joint, quadrant or bellows. The second connector 126 can have a built in duck-bill valve 128, and an escape valve 127 located on the second connector 126. This configuration is shown in U.S. Pat. No. 6,527,011 FIG. 3 and related disclosure (hereby specifically incorporated by reference).

Figure 9:
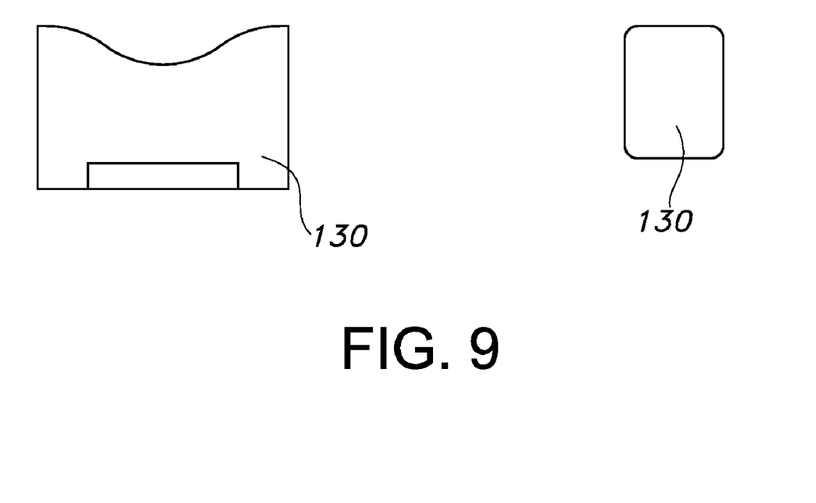
FIG. 9 is a front and side elevational view of the neck/back/head support device.

In addition, FIG. 9 shows a view of the neck, back and head support device. The tidal volume of this device ranges from 300-900 rn/i. Moreover, the cardiopulmonary resuscitation device 201 may include a wide elastic strip headband 131 for securing the face mask 19 around the patient's mouth and nose, etc.

Figure 3:
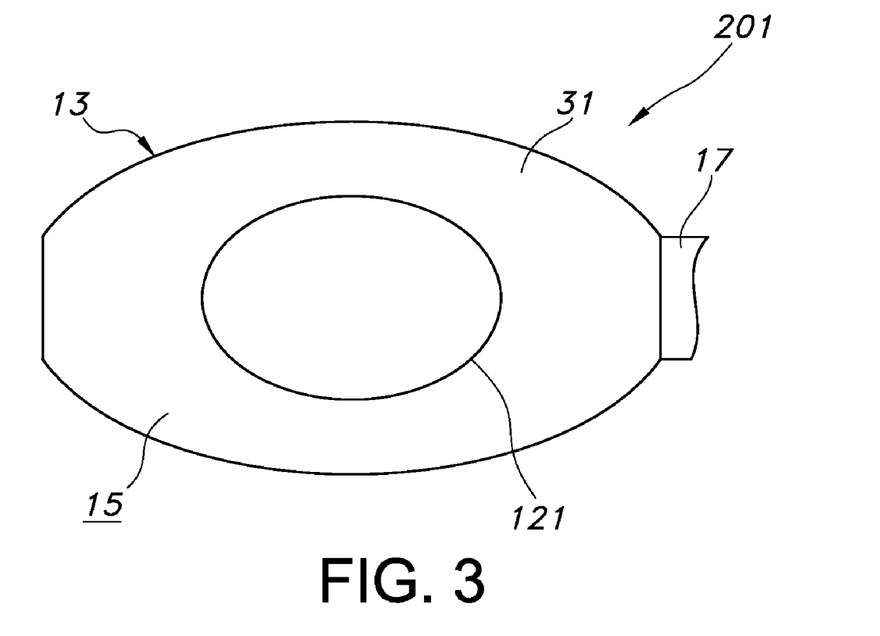
FIG. 3 is a top plan view of the self-inflating bag and a portion of the outlet port of the cardiopulmonary resuscitation device of the FIG. 1.
Figure 4:
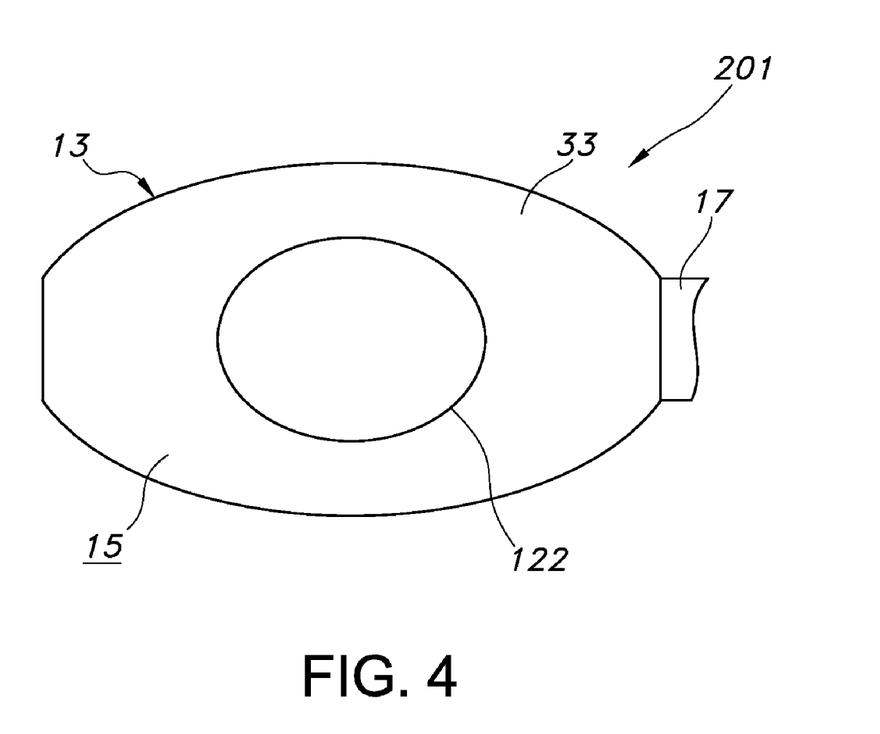
FIG. 4 is a bottom plan view of the self-inflating bag and a portion of the outlet port of the cardiopulmonary resuscitation device of the FIG. 1.
Figure 5:
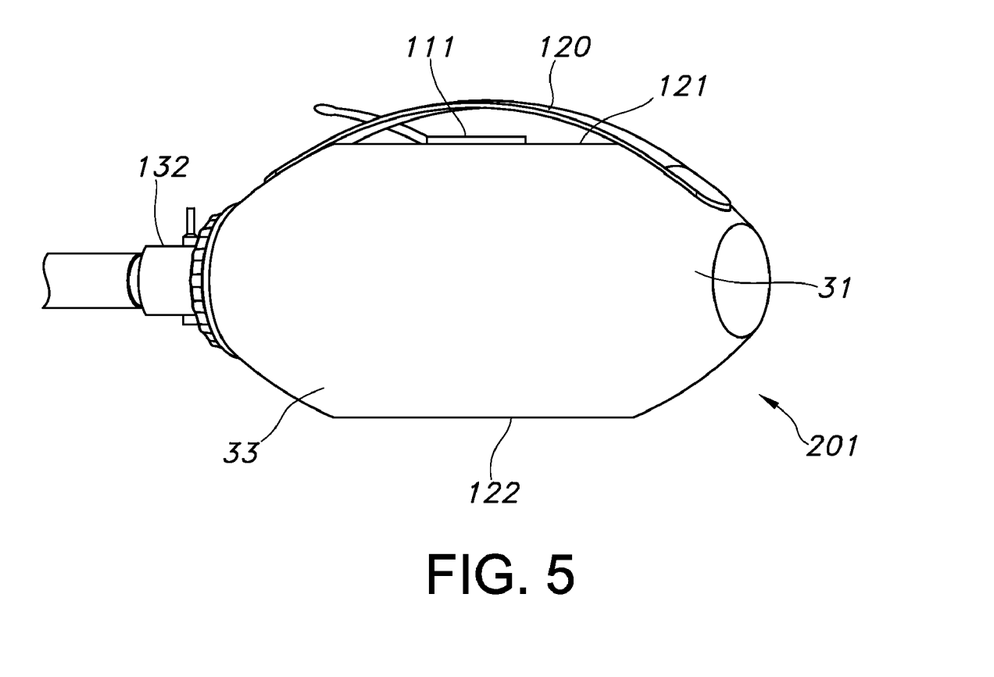
FIG. 5 is a side elevational view of the self-inflating bag of the cardiopulmonary resuscitation device of FIG. 1.
Figure 6:
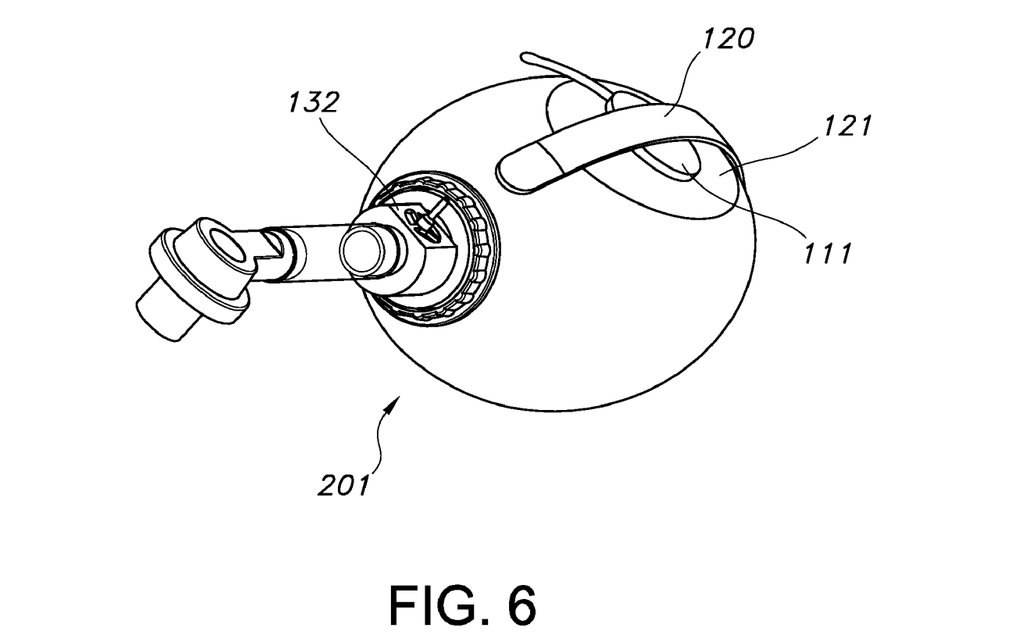
FIG. 6 is a view of the self-inflating bag of the cardiopulmonary resuscitation device of FIG. 1.

In addition, as shown in FIGS. 3 and 4, the cardiopulmonary resuscitation device 201 includes indicator means 111 for providing the user/rescuer R with an indicator of the amount of force being applied to the sternum area SA of the patent when applying force to the bottom 122 side of the bag 15. The top 121 of the resuscitator bag being flat will also allow for the chest compression indicator to fit evenly before and after each ventilation and chest compression.

The method of using the cardiopulmonary resuscitation device 201 of the present invention included the steps of first providing a cardiopulmonary resuscitation device 201 including a self-inflating bag 15, flat bottom side 122 on the self-inflating bag 15 to stably position the self-inflating bag on the patient's sternum area SA and to indicate the proper location on the self-inflating bag 15 for applying force to the flat top side 121. The user/rescuer R can then apply force to the flat top side 121 on the self-inflating bag 15 of the cardiopulmonary resuscitation device 201 to first force air from the self-inflating bat 15 through the tube 41 and the face mask 19. The flat top 121 and bottom 122 of the resuscitator bag 15 allow the bag 15 to be positioned on the patient without rolling off the sternum area, and it allows the user/rescuer to position his hand on the resuscitator bag evenly without slipping from the designated position.

Although the present invention has been described and illustrated with respect to a preferred embodiment and a preferred use therefore, it is not to be so limited since modifications and changes can be made therein which are within the full intended scope of the invention.

The invention claimed is:

1. A cardiopulmonary resuscitation device that combines artificial, emergency ventilation of a patient's lungs with chest compressions on the patient's sternum area, said cardiopulmonary resuscitation device comprising:
   a self-inflating bag having a non-rigid flat top side, a non-rigid flat bottom side for contacting the patient's sternum area wherein said self-inflating bag does not include a bag-fill valve;
   an outlet port through which the content of said self inflating bag is forced when said top side of said self-inflating bag is pushed toward said bottom side of said self-inflating bag;
   a first connector connecting the bag with a tube extending from said outlet port of said self-inflating bag to said face mask; wherein a bag-fill valve is positioned on said first connector,
   a face mask for placement over the patient's mouth and nose;
   indicator means contacting said self-inflating bag for placement over the patient's sternum area and for providing an indication of the amount of force being applied through top and bottom sides of said self-inflating bag to the patient's chest by said bottom side during chest compressions on the patient's sternum area when said top side of said self-inflating bag is pushed toward said bottom side of said self inflating bag.

2. The cardiopulmonary resuscitation device of claim 1 further comprising a second connector positioned between the tube and the face mask, wherein said second connector is flexible and air-tight.

3. The device of claim 2 further comprising a duck-bill valve incorporated into the second connector to prevent spent air from the patient lungs from entering the air tube.

4. The device of claim 2 further comprising an escape valve incorporated into the second connector through which the spent air from the patient to escape into the atmosphere.

5. A cardiopulmonary resuscitation device that combines artificial, emergency ventilation of a patient's lungs with chest compressions on the patient's sternum area, said cardiopulmonary resuscitation device comprising:
- a self-inflating bag having a non-rigid flat top side, a non-rigid flat bottom side for contacting the patient's sternum area wherein said self-inflating bag does not include a bag-fill valve;
- an outlet port through which the content of said self inflating bag is forced when said top side of said self-inflating bag is pushed toward said bottom side of said self-inflating bag;
- a first connector connecting the bag with a tube extending from said outlet port of said self-inflating bag to said face mask;
- a face mask for placement over the patient's mouth and nose;
- indicator means contacting said self-inflating bag for placement over the patient's sternum area and for providing an indication of the amount of force being applied through top and bottom sides of said self-inflating bag to the patient's chest by said bottom side during chest compressions on the patient's sternum area when said top side of said self-inflating bag is pushed toward said bottom side of said self inflating bag, further comprising a support device for supporting the back, neck, and head areas of a patient.

6. The cardiopulmonary resuscitation device of claim 5 further comprising a second connector positioned between the tube and the face mask, wherein said second connector is flexible and air-tight.

7. The device of claim 6 further comprising a duck-bill valve incorporated into the second connector to prevent spent air from the patient lungs from entering the air tube.

8. The device of claim 6 further comprising an escape valve incorporated into the second connector through which the spent air from the patient to escape into the atmosphere.

9. A cardiopulmonary resuscitation device that combines artificial, emergency ventilation of a patient's lungs with chest compressions on the patient's sternum area, said cardiopulmonary resuscitation device comprising:
- a self-inflating bag having a non-rigid flat top side, a non-rigid flat bottom side for contacting the patient's sternum area wherein said self-inflating bag does not include a bag-fill valve;
- an outlet port through which the content of said self inflating bag is forced when said top side of said self-inflating bag is pushed toward said bottom side of said self-inflating bag;
- a first connector connecting the bag with a tube extending from said outlet port of said self-inflating bag to said face mask;
- a face mask for placement over the patient's mouth and nose wherein a bag-fill valve is positioned on said face mask;
- indicator means contacting said self-inflating bag for placement over the patient's sternum area and for providing an indication of the amount of force being applied through top and bottom sides of said self-inflating bag to the patient's chest by said bottom side during chest compressions on the patient's sternum area when said top side of said self-inflating bag is pushed toward said bottom side of said self inflating bag.

10. The cardiopulmonary resuscitation device of claim 9 further comprising a second connector positioned between the tube and the face mask, wherein said second connector is flexible and air-tight.

11. The device of claim 10 further comprising a duck-bill valve incorporated into the second connector to prevent spent air from the patient lungs from entering the air tube.

12. The device of claim 10 further comprising an escape valve incorporated into the second connector through which the spent air from the patient to escape into the atmosphere.

\* \* \* \* \*